United States Patent
Joshi et al.

(10) Patent No.: US 8,262,872 B2
(45) Date of Patent: Sep. 11, 2012

(54) CLEANSING AGENT GENERATOR AND DISPENSER

(75) Inventors: Ashok V. Joshi, Salt Lake City, UT (US); Shekar Balagopal, Sandy, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 912 days.

(21) Appl. No.: 12/172,954

(22) Filed: Jul. 14, 2008

(65) Prior Publication Data

US 2008/0264778 A1 Oct. 30, 2008

Related U.S. Application Data

(63) Continuation-in-part of application No. 11/613,857, filed on Dec. 20, 2006.

(60) Provisional application No. 60/753,191, filed on Dec. 20, 2005, provisional application No. 60/949,802, filed on Jul. 13, 2007.

(51) Int. Cl.
*C25B 9/08* (2006.01)
*C25B 9/10* (2006.01)

(52) U.S. Cl. .................. 204/266; 204/252; 204/263

(58) Field of Classification Search .............. 205/500, 205/620, 687; 204/252, 263, 266
See application file for complete search history.

(56) References Cited

U.S. PATENT DOCUMENTS

| | | | |
|---|---|---|---|
| 2,636,852 A | 4/1953 | Juda et al. | |
| 3,925,174 A | 12/1975 | Eng et al. | |
| 5,290,405 A | 3/1994 | Joshi et al. | |
| 5,362,368 A | 11/1994 | Lynn et al. | |
| 5,580,430 A | 12/1996 | Balagopal et al. | |
| 5,935,393 A | 8/1999 | Shinomiya et al. | |
| 6,174,419 B1 | 1/2001 | Akiyama | |
| 6,703,153 B1 | 3/2004 | Cubukcu et al. | |
| 6,719,891 B2* | 4/2004 | Ruhr et al. | 205/500 |
| 6,805,787 B2 | 10/2004 | Bess et al. | |
| 2003/0098244 A1 | 5/2003 | Ruhr et al. | |
| 2004/0267190 A1 | 12/2004 | Tamarkin et al. | |
| 2005/0177008 A1* | 8/2005 | Balagopal et al. | 568/851 |
| 2006/0226022 A1 | 10/2006 | Balagopal et al. | |
| 2007/0012570 A1 | 1/2007 | Carus et al. | |
| 2007/0138020 A1 | 6/2007 | Balagopal et al. | |

(Continued)

FOREIGN PATENT DOCUMENTS

DE 10360758 7/2005

(Continued)

OTHER PUBLICATIONS

Young, Lee "International Search Report", International Application No. PCT/US 08/08623, (Oct. 1, 2008), 1-2.

(Continued)

*Primary Examiner* — Bruce Bell
(74) *Attorney, Agent, or Firm* — David Fonda

(57) ABSTRACT

Electrochemical apparatus and processes for the point-of-use production of cleansing, sanitizing, and antimicrobial agents, such as sodium hypochlorite (NaOCl) or hypochlorous acid (HOCl). The processes may be used to produce NaOCl from seawater, low purity un-softened or NaCl-based salt solutions. HOCl may be produced from HCl solutions and water. NaOCl is produced using a sodium ion conductive ceramic membrane, such as membranes based on NASICON-type materials, in an electrolytic cell. HOCl is produced using an anion conductive membrane in an electrolytic cell. The cleansing, sanitizing, and antimicrobial agent may be generated on demand and used in household, industrial, and water treatment applications.

14 Claims, 5 Drawing Sheets

U.S. PATENT DOCUMENTS

| | | | |
|---|---|---|---|
| 2007/0141434 | A1 | 6/2007 | Joshi et al. |
| 2008/0142373 | A1 | 6/2008 | Joshi et al. |
| 2008/0173540 | A1 | 7/2008 | Joshi et al. |
| 2008/0173551 | A1 | 7/2008 | Joshi et al. |
| 2008/0245671 | A1 | 10/2008 | Balagopal et al. |

FOREIGN PATENT DOCUMENTS

| | | |
|---|---|---|
| EP | 0559400 | 9/1993 |
| EP | 0826794 | 3/1998 |

OTHER PUBLICATIONS

Young, Lee "Written Opinion of the International Searching Authority", International Application No. PCT/US 08/08623, (Oct. 1, 2008), 1-5.

Sutija, Davor et al., "Ceramic cleansers: Environmental Uses of Sodium Super-Ionic Conducting Ceramics", *The Electrochemical Society Interface*, Winter 1996, vol. 5. No. 4,26-30.

Balagopal, S. et al., "Selective Sodium Removal From Aqueous Waste Streams with NaSICON Ceramics ", *Separation and Purification Technology*, 15 (1999), 231-237.

Goodenough, J.B. et al., "Fast Na+ -Ion Transport in Skeleton Structures", *Mat. Res. Bull.*, vol. 11. Pergamon Press, Inc. Printed in the United States, (1976), 203-220.

Hong, H.Y-P. et al., "Crystal Structures and Crystal Chemistry in the System $Na_{1+x}Zr_2Si_xP_{3-x}O_{12}$", *Mat. Res. Bull.*, vol. 11. 1976. Pergamon Press, Inc. Printed in the United States., (1976), 173-186.

Bentzen, J. J., et al., "The Preparation and Characterization of dense, highly conductive $Na_5GdSi_4O_{12}$ nasicon (NGS)", *Materials Research Bulletin*, vol. 15, (1980). 1737-1745.

Delmas, C. et al., "Crystal chemistry of the $Na_{1+x}Zr_{2-x}L_x(PO_4)_3$(L=Cr, In, Yb) solid solutions", *Materials Research Bulletin*, vol. 16, (1981), 285-290.

Von Alpen, V. et al., "Compositinal dependence of the electrochemical and structural parameter in the NASICON system $(Na_{1+x}Si_xZr_2P_{3-x}O_{12})$", *Solid State Ionics*, vol. 3/4, (1981), 215-218.

Fujitsu, S. et al., "Conduction Paths in sintered ionic conductive material $Na_{1+x}Y_xZr_{2-x}(PO_4)_3$", *Materials Research Bulletin*, vol. 16(1981), 1299-1309.

Saito, Y. et al., "Ionic Conductivity of NASICON-type conductors $Na_{1.5}M_{0.5}Zr_{1.5}(PO_4)_3$(M: $Al^{3+}$,$Ga^{3+}$, $Cr^{3+}$, $Fe^{3+}$, $In^{3+}Yb^{3+}$, $Y^{3+}$)", *Solid State Inonics*, vol. 58, (1992), 327-331.

Alamo, J. "Chemistry and properties of solids with the [NZP]skeleton", *Solid State Ionics*, vol. 63-65, (1993), 547-561.

Shimazu, K. et al., "Electrical conductivity and $Ti^{4+}$ ion substitution range in NASICON system ", *Solid State Ionics*, vol. 79, (1995), 106-110.

Miyajima, Y. et al., "Ionic conductivity of NASICON-type $Na_{1+x}M_xZr_{2-x}P_3O_{12}$(M: Yb, Er, Dy)", *Solid State Ionics*, vol. 84,(1996), 61-64.

Lehmann, Thomas et al., "Abstract of DE10360758", DE10360758, (Jul. 28, 2005), 1-2.

Young, "PCT/US06/48746 International Search Report", (Oct. 1, 2007), 1-2.

Young, "PCT/US06/48746 Written Opinion", (Oct. 1, 2007), 1-4.

Gregg, Nicholas "European Search Report", European Application No. 06847897.3 PCT App. No. PCT/US2006048746, (Sep. 16, 2009), 1-4.

Jo, Soo "Written Opinion of the International Searching Authority", International App. No. PCT/US2009/054953, (Mar. 31, 2010), 1-4.

Jo, Soo "International Search Report", International App. No. PCT/US2009/054953, (Mar. 31, 2010), 1-3.

Jo, Soo "Written Opinion of the International Searching Authority", International App. No. PCT/US2009/054966, (Apr. 1, 2010), 1-4.

Jo, Soo "International Search Report", International Application No. PCT/US2009/054966, (Apr. 1, 2010), 1-3.

Gamez, Agnes "Supplementary European Search Report", Search Report and Opinion for European Patent Application #EP08794491. 4, 1-5.

Friday, Steven "Non-Final Office Action", Non-final Action for U.S. Appl. No. 12/547,334, pp. 1-11.

Kunigata, Yasunobu "Notice of reasons for rejection", Translation of Japanese office action for JP application #2008/547536 (corresponding to U.S. Appl. No. 11/613,857), 1-4.

Bell, Bruce "Office Ation", Non-Final Office Action for U.S. Appl. No. 11/613,857, 1-8.

Bell, Bruce "Office Action", Final Office Action for U.S. Appl. No. 11/613,857, 1-9.

Bell, Bruce "Office Action", Final Office Action for U.S. Appl. No. 11/613,857, 1-13.

Bell, Bruce "Office Action", Non-Final Office Action for U.S. Appl. No. 11/613,857, 1-11.

* cited by examiner

CLEANSING AGENT GENERATOR AND DISPENSER

CROSS-REFERENCE TO RELATED APPLICATION

This application is a continuation-in-part of U.S. patent application Ser. No. 11/613,857, filed Dec. 20, 2006, which claims the benefit of U.S. Provisional Patent Application No. 60/753,191, filed Dec. 20, 2005, both of which are incorporated by reference. This application also claims the benefit of U.S. Provisional Patent Application No. 60/949,802, filed Jul. 13, 2007, which is incorporated by reference.

FIELD OF THE INVENTION

The present invention relates to a point-of-use electrochemical generator and dispenser of cleansing, sanitizing, and antimicrobial agents.

BACKGROUND OF THE INVENTION

Household appliances (e.g. dishwashers, clothes washers, etc.) have a need for disinfectants, bleaching solutions, whiteners, deodorizers, or in other words, a cleansing agent. Common surfaces often require cleansing or sanitizing. It would be an advancement to provide an apparatus for generating and dispensing cleansing, sanitizing, and antimicrobial agents as needed for appliances or surfaces that may require such agents.

In some methods, sodium hypochlorite is prepared by absorbing chlorine gas into cold sodium hydroxide solution to induce the following reaction:

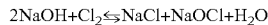

The sodium hydroxide and chlorine reagents input into this process may be commercially produced by the chloralkali process. For use in this reaction, there is generally no need to isolate the reagents, thus, NaOCl may be prepared in an industrial setting by electrolyzing sodium chloride solution without any separation or barrier between the anode and the cathode. In this process, the reaction solution is generally maintained at a temperature below about 40° C. in order to prevent the formation of sodium chlorate. As a result, commercially-prepared sodium hypochlorite solutions generally contain amounts of sodium chloride as a primary byproduct.

Hypochlorous acid (also known as chloric(I) acid) is a weak acid with the chemical formula HClO. HClO is used as a bleach, an oxidizer, a deodorant, and a disinfectant. HClO has been approved by the U.S. FDA for use on food in washing and cleaning applications. HClO has also been approved for use on human skin as a cleansing and sanitizing agent. It is also reported to promote wound healing. Addition of chlorine to water gives both hypochlorous acid and hydrochloric acid (HCl):

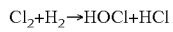

Hypochlorous acid cannot be isolated in pure form due to rapid equilibration with the anion hypochlorite (OCl⁻) and hydrogen ion (H⁺):

It would be an advancement in the art to provide an apparatus and method to generate sodium hypochlorite (NaOCl) or hypochlorous acid (HOCl) on demand. Other known methods require the storage and transport of sodium hydroxide and of chlorine gas which is a highly toxic substance. The present invention overcomes this problem using electrochemical processes for the production of sodium hypochlorite or hypochlorous acid. More particularly, the present invention provides an electrochemical process for producing sodium hypochlorite or hypochlorous acid using readily available and safe starting materials.

BRIEF SUMMARY OF THE INVENTION

The present invention is drawn to an electrochemical apparatus and method to generate and dispense a cleansing, sanitizing, or antimicrobial agent on demand and at the point-of-use (POU). The present invention in particularly adapted for use with household, industrial, and water treatment applications. Using common table salt (NaCl), salt water, waste streams from certain products, or other feed stocks; a moderate amount of electricity; and the proper apparatus it is possible to generate sodium hypochlorite (NaOCl) or hypochlorous acid (HOCl) on an as needed basis. These compounds can serve as cleansing, sanitizing, or antimicrobial agents. They may even function as bleach for removal of stains. Other methods for formation of these compounds need the transport and storage of chlorine gas which is a highly toxic material. Because HOCl is not stable for long-term storage, the ability to generate these compounds at suitable concentrations at the point of use is particularly advantages.

In one embodiment, a cleansing, sanitizing, or antimicrobial agent, collectively referred to as a cleansing agent, is generated and used in various types of apparatuses such as a washing machine, a dishwasher, a scrub brush, a floor brush or mop, a toilet bowl apparatus, skin patch, or any application where a dose of a cleansing agent is desired.

Sodium hypochlorite (NaOCl) may be effectively generated using an electrolytic process using a sodium ion conductive ceramic membrane, such as a sodium super ionic conductor (hereinafter "NaSICON") membrane. Copending U.S. patent application Ser. No. 11/613,857, Published as US 2007/0138020A1 and incorporated herein by reference, discloses electrolytic processes to produce sodium hypochlorite using sodium ion conduction ceramic membranes. In this process, sodium is extracted from a solution of sodium chloride (<3 weight %). The extracted sodium reacts with water on the other side of the membrane to form a slightly basic solution of sodium hydroxide (NaOH) with a pH in the range of 7-8. The sodium hydroxide can in turn be reacted with chloride to form sodium hypochlorite.

Hypochlorous acid (HOCl) may be prepared using an electrolytic process using an anionic conductive membrane. In this process, chloride ions are extracted from a solution containing chloride ions, such as dilute hydrochloric acid. The extracted chloride ions react with water on the other side of the membrane to form a solution of hypochlorous acid and hydrochloric acid.

In one embodiment, a cleansing agent generator is an electrochemical cell. The electrochemical cell can be configured in a variety of ways to produce the cleansing agent. In one embodiment, cationic membranes are utilized that may be selective to only certain types of cations. The cations move across the membrane when voltage is applied across the electrodes of electrochemical cell. In another embodiment, an anionic membrane which can transport anions, such as chloride, is used.

The cleansing agent distributor may be configured in numerous forms depending on the point-of-use application for the cleansing agent. Examples of such forms, include but are not limited to, personal and household applications such as a washing machine, a dishwasher, a scrub brush, a floor brush or mop, a toilet bowl apparatus, and a skin patch; industrial applications such as water treatment systems, public sanitizing applications in hospitals, hotels, schools, ocean vessels, and in applications where cleansing, sanitizing, or antimicrobial agent are used.

Other advantages and aspects of the present invention will become apparent upon reading the following description of the drawings and detailed description of the invention. These and other features and advantages of the present invention will become more fully apparent from the following figures, description, and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the point-of-use electrochemical generator and dispenser of cleansing, sanitizing, and antimicrobial agents, as represented in FIGS. 1 through 6, is not intended to limit the scope of the invention, as claimed, but is merely representative of presently preferred embodiments of the invention.

The phrase "substantially impermeable to water," when used in the instant application to refer to a membrane, means that a small amount of water may pass through the membrane, but that the amount that passes through is not of a quantity to diminish the usefulness of the present invention. The phrase "essentially impermeable to water," as used herein in reference to a membrane, means that no water passes through the membrane, or that if water passes through the membrane, its passage is so limited so as to be undetectable by conventional means. The words "substantially" and "essentially" are used similarly as intensifiers in other places within this specification.

Figure 1:
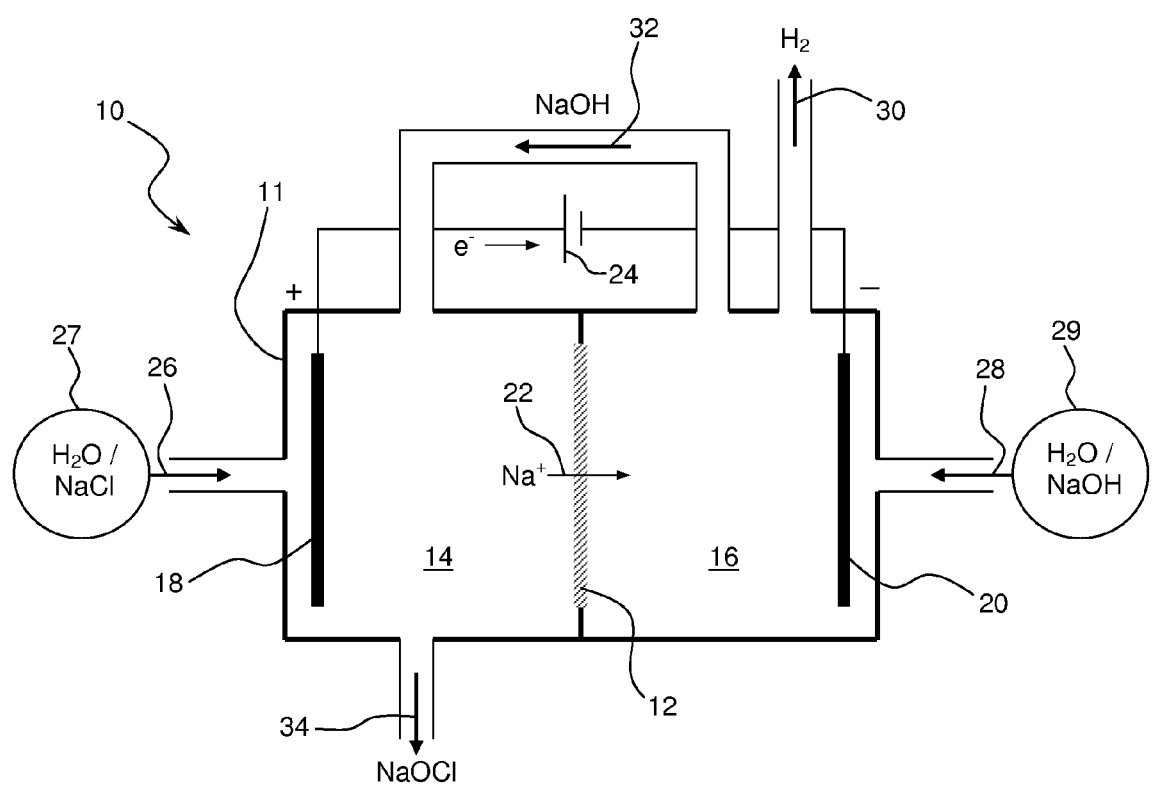
FIG. 1 is a schematic view of an embodiment of a cleaning agent generator that may be used to produce sodium hypochlorite within the scope of the present invention.

FIG. 1 illustrates a cleansing agent generator 10 that may be used to produce sodium hypochlorite. The cleansing agent generator 10 comprises an electrolytic cell 11 that uses a sodium ion conductive ceramic membrane 12 that divides the electrochemical cell 10 into two compartments: an anolyte compartment 14 and a catholyte compartment 16. An electrochemically active anode 18 is housed in the anolyte compartment 14 where oxidation reactions take place, and an electrochemically active cathode 20 is housed in the catholyte compartment 16 where reduction reactions take place. The sodium ion conductive ceramic membrane 12 selectively transfers sodium ions 22 from the anolyte compartment 14 to the catholyte compartment 16 under the influence of an electrical potential 24 while preventing water transportation from either compartment to the other side.

The electrolytic cell 11 is operated by feeding an aqueous sodium chloride solution 26 into the anolyte compartment 14 from a feeder 27. The sodium chloride solution 26 may come from any source, including naturally occurring seawater or brine sources. The sodium chloride solution may be prepared by dissolving salt containing sodium chloride in water. The water need not be pure de-ionized water, but it can be tap water or unpurified water from any source. The concentration of sodium chloride in the aqueous solution should be below its saturation limit in water. The concentration of sodium chloride in the aqueous solution is between about 0.1% by weight and about 26% by weight of the solution, and more preferably between about 3% by weight and 26% by weight of the solution.

Water 28 is fed into the catholyte compartment 16 from feeder 29. At least initially, the water 28 preferably includes sodium ions, which may be in the form of an unsaturated sodium hydroxide solution. The concentration of sodium hydroxide is between about 0.1% by weight and about 50% by weight of the solution. In one embodiment, the water 28 includes a dilute solution of sodium hydroxide. During operation, the source of sodium ions may be provided by sodium ions 22 transporting across the sodium ion conductive ceramic membrane 12 from the anolyte compartment 14 to the catholyte compartment 16.

The anode 18 may be fabricated of various materials, including those discussed in U.S. Patent Application Publication No. 2007/0138020, incorporated by reference. In one embodiment, the anode 18 is fabricated of titanium coated with advanced metal oxides. The cathode 20 may also be fabricated of various materials, including those discussed in U.S. Patent Application Publication No. 2007/0138020. In one embodiment, the cathode 20 is fabricated of nickel/stainless steel. Under the influence of electric potential 24, electrochemical reactions take place at the anode 18 and cathode 20. Oxidation of chloride ions to chlorine gas occurs at the anode 18, and reduction of water to form hydrogen gas 30 and hydroxyl ions occurs at the cathode 20.

As the reactions occur at the electrodes, sodium ions 22 are transported from the anolyte compartment 14 across the sodium ion conductive ceramic membrane 12 into the catholyte compartment 16. If non-sodium ions, such as protons, calcium, magnesium, etc, are also present in the anolyte compartment 14, they are prevented from moving to the catholyte compartment 16 by the solid electrolyte 12 due to ionic size differences and electroneutrality constraints when compared with the sodium ions. Due to this reason, the current sodium efficiency is expected to be between from about 95 to about 100% in some embodiments. The transported sodium ions 22 combine with the hydroxyl ions produced by the reduction of water at the cathode 20 to form a sodium hydroxide solution. Part of this sodium hydroxide solution 32 is transported to the anolyte compartment 14 of the cell to control anolyte pH and produce sodium hypochlorite solution. Sodium hypochlorite solution 34 may be removed from the anolyte compartment 14. The solution comprising sodium hypochlorite is removed from the anolyte compartment 14 for on-site or point-of-use. As used herein, the term point-of-use refers to use of the produced cleansing agent in a personal, commercial or industrial process located proximate to the cleansing agent generator, so that expensive storage or transportation facilities for the cleansing agent are not required.

The chemical reactions in the electrochemical cell 11 are summarized below:

At the anode/
anolyte compartment: $2Cl^- \rightarrow Cl_2 + 2e^-$ $$Cl_2 + H_2O \rightarrow HOCl + HCl$$

$$HOCl + HCl + 2NaOH \rightarrow NaOCl + NaCl + 2H_2O$$

At the cathode/
catholyte compartment: $2H_2O + 2e^- \rightarrow 2OH^- + H_2$ $$2Na^+ + 2OH^- \rightarrow 2NaOH$$

Overall reaction: $2NaCl + H_2O \rightarrow NaOCl + NaCl + H_2$

The pH control of the anolyte solution is especially important when feed to the anolyte solution is an impure sodium chloride solution containing calcium, magnesium, or other precipitable cations. Such sodium chloride solutions include, but are not limited to, seawater, brine, industrial process streams, or salt solutions containing sodium chloride. Such salt solutions may be prepared with pure or impure salt or with pure or impure water. The pH of the solution within the anolyte compartment 14 is preferably maintained at a pH less than 14, usually in preferred pH in the range from 7 to 12. Because calcium and magnesium precipitate at a pH greater than about 8, it is preferred to maintain the pH less than about 8 when operating with impure sodium chloride solutions. For pure sodium chloride solutions, the anolyte solution may have higher pH. With pH control, precipitation reactions at the anode, formation of calcium and magnesium hydroxides, may be avoided, thereby producing a clear solution of sodium hypochlorite.

The sodium conductive ceramic membrane 12 preferably blocks diffusion of calcium or magnesium ions to the catholyte compartment 16 during electrolysis. Thus, precipitation of calcium and magnesium is avoided in the catholyte compartment. In contrast, precipitation is unpreventable with organic membranes, such as Nafion® membranes, as they are, unlike NaSICON membranes, not able to completely prevent the diffusion of calcium and magnesium ions to the catholyte compartment 16, causing precipitation of calcium and magnesium not only in the catholyte compartment 16 but also in the interstices of membrane, gradually eroding the membrane's effectiveness. This drawback of the organic membranes limits their use in sodium hypochlorite generation to only salt solution feeds containing just sodium chloride.

The voltage required by the electrolytic cell 11, at constant current, is dependent on factors such as concentration of anolyte (sodium chloride solution), concentration of catholyte (sodium hydroxide solution), membrane thickness, conductivity of the membrane, and local mass transfer conditions which dictate the electrolytic cell's power consumption for a given production rate of sodium hypochlorite.

Figure 2:
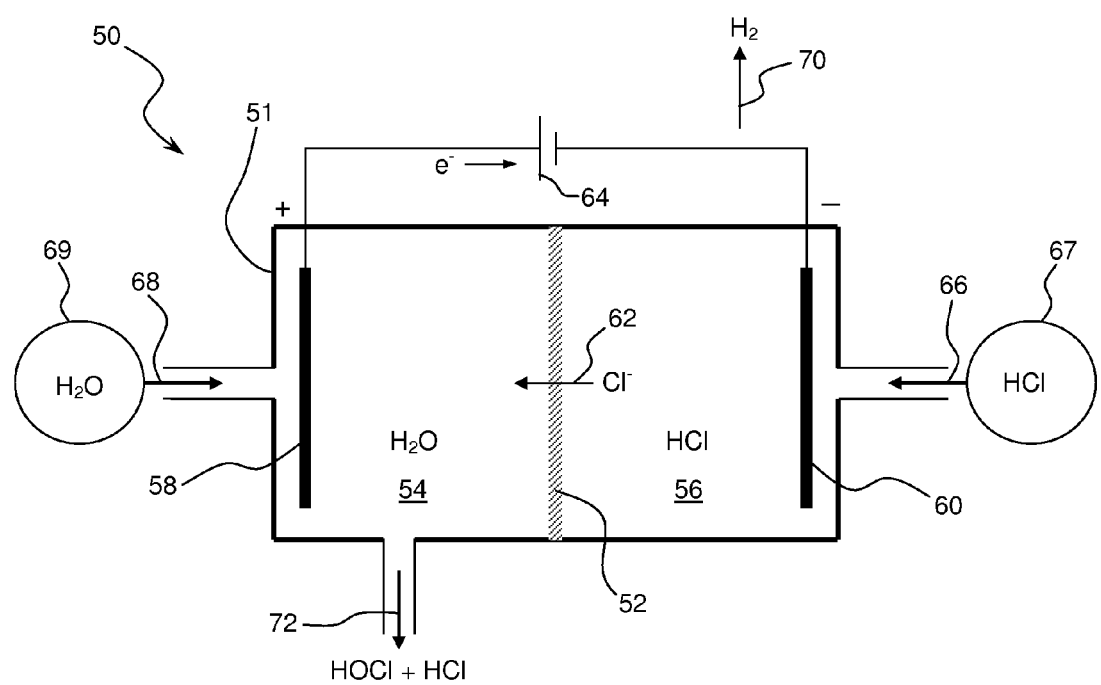
FIG. 2 is a schematic view of an embodiment of a cleaning agent generator that may be used to produce hypochlorous acid within the scope of the present invention.

FIG. 2 illustrates a cleansing agent generator 50 that may be used to produce hypochlorous acid (HClO). The cleansing agent generator 50 comprises an electrolytic cell 51 that uses an anion conductive membrane 52 that divides the electrochemical cell 51 into two compartments: an anolyte compartment 54 and a catholyte compartment 56. An electrochemically active anode 58 is housed in the anolyte compartment 54 where oxidation reactions take place, and an electrochemically active cathode 60 is housed in the catholyte compartment 56 where reduction reactions take place. The anion conductive membrane 52 selectively transfers chloride ions 62 from the catholyte compartment 56 to the anolyte compartment 54 under the influence of an electrical potential 64.

The electrolytic cell 51 is operated by feeding a dilute hydrochloric acid (HCl) solution 66 into the catholyte compartment 56 from a feeder 67. The water need not be pure de-ionized water, but it can be tap water or unpurified water from any source.

Water 68 is fed into the anolyte compartment 54 from feeder 69. During operation, the source of chloride ions that react at the anode to form chlorine may be provided by chloride ions 62 transporting across the anion conductive membrane 62 from the catholyte compartment 56 to the anolyte compartment 54.

The anode 58 and cathode 60 may be fabricated of various materials, including those discussed above and in U.S. Patent Application Publication No. 2007/0138020. Under the influence of electric potential 64, electrochemical reactions take place at the anode 58 and cathode 60. Oxidation of chloride ions to chlorine gas occurs at the anode 58, and reduction of water to form hydrogen gas 70 and hydroxyl ions occurs at the cathode 60.

As the reactions occur at the electrodes, chloride ions 62 are transported from the catholyte compartment 56 across the anion conductive membrane 52 into the anolyte compartment 54. The transported chloride ions 62 react at the anode 58 to form chlorine which reacts with water to form to form a hypochlorous acid solution 72. Hypochlorous acid solution 72 may be dispensed from the anolyte compartment 54 for on-site or point-of-use into a device or apparatus such those described herein.

The chemical reactions in the electrochemical cell 51 are summarized below:

At the anode/
anolyte compartment: $2Cl^- \rightarrow Cl_2 + 2e^-$ $$Cl_2 + H_2O \rightarrow HOCl + HCl$$

At the Cathode/
catholyte compartment: $2H^+ + 2e^- \rightarrow H_2$

Overall reaction: $2HCl + H_2O \rightarrow HOCl + HCl + H_2$

The pH control of the anolyte solution is important to promote formation of HOCl. The pH of the solution within the anolyte compartment 54 is preferably maintained at a pH less than 11, usually with a preferred pH in the range from 5 to 11, and more preferably between 6 and 8. With a pH less than 5, HCl formation is favored over HOCl.

The anion conductive membrane 52 as employed herein is defined to include membranes which have selective permeability, i.e., permselectivity, by allowing passage of chloride anions (Cl⁻), but not cations. Anion conductive membranes may be strongly, mildly or weakly basic, and may be comprised of quaternary or tertiary ammonium groups, for example. Anion conductive membranes should be stable in the electrolytic environment and have a low resistance to the anion being transported.

Anion conductive membranes may include commercially available anion exchange membranes. Representative anion exchange membranes include polystyrene-polydivinyl-benzene polymeric base materials, such as Tokuyama Neosepta AMH or Asahi Glass Selemion AMV, and perfluorinated radiation grafted materials, such as Pall Raipore. Solvay Morgane products may also be used.

The cleansing agent generators described herein can be operated in a continuous or batch mode. In one embodiment of the processes and apparatus of the present invention, the cleansing agent generator may be operated in a continuous mode. In a continuous mode, the electrolytic cell is initially filled with anolyte and catholyte solutions and then, during operation, additional solutions are fed into the cell and products, by-products, and/or diluted solutions are removed from the cell without ceasing operation of the cell. The reactant solutions may be fed into the anolyte and catholyte compartments continuously or they may be fed intermittently, meaning that the flow of a given solution is initiated or stopped according to the need for the solution and/or to maintain desired concentrations of solutions in the cell, without emptying one or both compartments. Similarly, the removal of solutions from the anolyte compartment and the catholyte compartment may also be continuous or intermittent.

Control of the addition and/or removal of solutions from the cleansing agent generator may be done by any suitable means. Such means include manual operation, such as by one or more human operators, and automated operation, such as by using sensors, electronic valves, laboratory robots, etc. operating under computer or analog control. In automated operation, a valve or stopcock may be opened or closed according to a signal received from a computer or electronic controller on the basis of a timer, the output of a sensor, or other means. One non-limiting example of an automated control system is illustrated schematically in FIG. 3 and discussed below. Some combination of manual and automated operation may also be used. Alternatively, the amount of each solution that is to be added or removed per unit time to maintain a steady state may be experimentally determined for a given electrolytic cell, and the flow of solutions into and out of the system set accordingly to achieve the steady state flow conditions.

Figure 3:
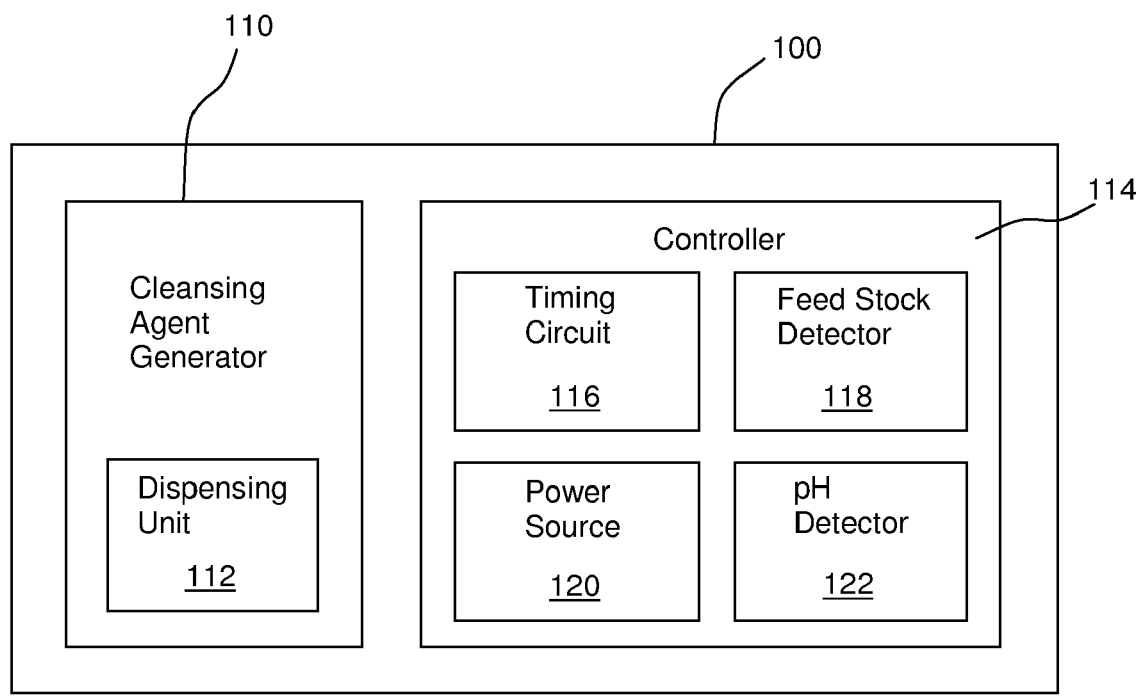
FIG. 3 is a is a schematic view of a cleansing agent disbursement system within the scope of the present invention.

FIG. 3 shows a non-limiting schematic drawing of a cleansing agent dispersement system 100. A cleansing agent generator 110, of the type mentioned above in connection with FIGS. 1 and 2 may be used. The cleansing agent generator 110 may be an electrochemical cell of the type known in the art. It could be configured with an anode in an anolyte compartment and a cathode in a catholyte compartment. The amount and content of material in each compartment along with the type of selective membrane is determined based upon the desired cleansing agent to be output. As power is supplied to the system, the electrochemical cell generates the cleansing agent which is then dispensed by the dispensing unit 112. The dispensing unit 112 may include various types of conduits, and may be used in conjunction with a variety of valves or pumps to control the release of the cleansing agent according to known fluid handling systems.

A controller 114 may include a timing circuit module 116, a feed stock detector module 118, a power source module 120, and/or a pH detector module 122. These modules could include software, hardware, firmware, instruction codes, and the like. The controller 114 may determine whether enough cleansing agent has been produced, whether certain parameters of the cleansing agent have been met, such as pH, temperature, content, concentration, and the like. The controller 114, working with or without the apparatus that will utilize the cleansing agent, may determine when to disperse the cleansing agent. The controller may also control the power source and vary the current applied to the electrochemical cell to thereby control the rate and amount of cleansing agent generated. As cleansing agent is generated, one or more feeders may resupply one or more of the catholyte compartment or anolyte compartment of the electrochemical cell. The controller may detect levels within each compartment of the electrochemical cell in order to replenish it and also the levels of the feeder reservoirs. The system 100 may have an audio or visual output (not shown) that conveys to a user the status of the system. The status may include whether the cleansing agent has been generated, whether and when it has be dispersed, pH, concentration, or temperature warnings, levels of feed stock available, and the like. Also, the controller may notify a user of the need to replenish the salt solution into the cell.

Figure 4:
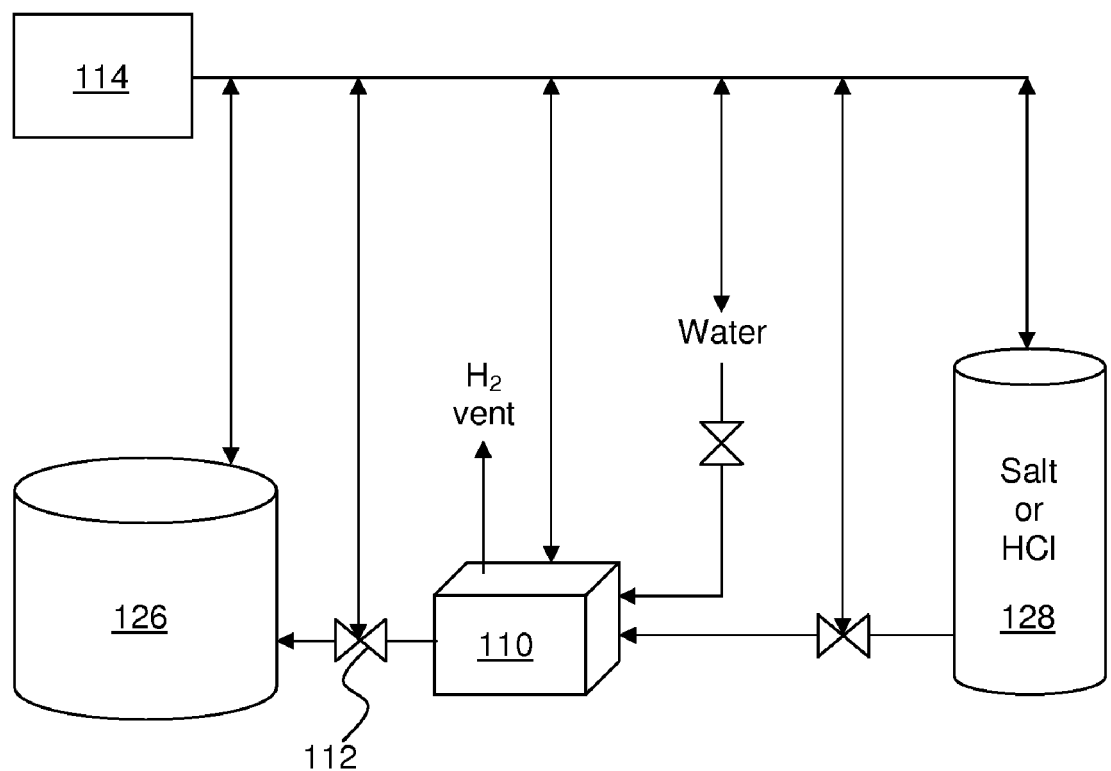
FIG. 4 is a is a schematic view of a cleansing agent disbursement system applied to a washing machine.

FIG. 4 illustrates a non-limiting example where the controller 114 may control when cleansing agents are dispersed into a washing machine 126. While FIG. 4 is illustrated and discussed in relation to a washing machine, it will be appreciated that other appliances may be used in place of the washing machine. When a user starts the washing machine 126, the controller 114 may detect whether the cleansing agent generator 110 comprising an electrochemical cell (EC) contains the proper contents to make the desired cleansing agent. If the EC does not contain the proper contents, the controller automatically fills each compartment with the desired material. In one embodiment, it could be a salt or HCl solution 128. In another embodiment, the feedstock could be a powder or solid and the system utilizes water from the washing machine to make the right solution either in the EC, or before it is deposited in the EC. The controller, taking an electric or other signal from the washing machine 126, applies power to the electrochemical cell so that it generates the cleansing agent. At a predetermined time, the cleansing agent is dispersed into the washing machine 126. Where the cleansing agent is bleach, the controller 114 may wait until a particular rinse or fill cycle in order apply the proper cleaning effect without damaging or discoloring the clothes. Unused cleansing agent, source material, or by products may then be removed from the EC. Gaseous byproducts such as hydrogen may be vented from the EC. The reservoir feeder may then refill the EC. As shown in FIG. 4, the controller 114 may be coupled to the various components of the system, including the washing machine 126, cleansing agent generator 110, valves and sensors, including dispensing unit 112, feeders, and such as feedstock source 128.

One suggested application of the apparatus illustrated in FIG. 4 is to generate NaOCl as a part of an apparatus to provide bleaching agent to a washing machine. In this embodiment an electronic control system would generate a solution of NaOCl (<5 weight %) and introduce that solution into the wash water at an appropriate time in the wash cycle. The percentage of NaOCl could be varied dependent upon the temperature, fabric, and agitation selections. The gradual introduction of the sodium hypochlorite would prevent any damage to fabrics.

A second non-limiting application would be to generate NaOCl as part of an apparatus to provide disinfectant to a dishwasher. In this embodiment an electronic control system would signal the generator to produce a solution of NaOCl (~0.5 weight %) as a final step in the process to insure the dishes were adequately disinfected.

A third non-limiting application would be to generate NaOCl on board a ship to generate disinfectant on an as needed basis. In this embodiment, salt water could serve as the input if the ship were located in the ocean. This has the potential to reduce the spread of infectious bacteria as has occurred on cruise ships in the past. Obviously, the generator could also be incorporated with numerous portions of the ship's apparatus (e.g. washing machine, dishwasher, reverse osmosis system, etc).

Figure 5:
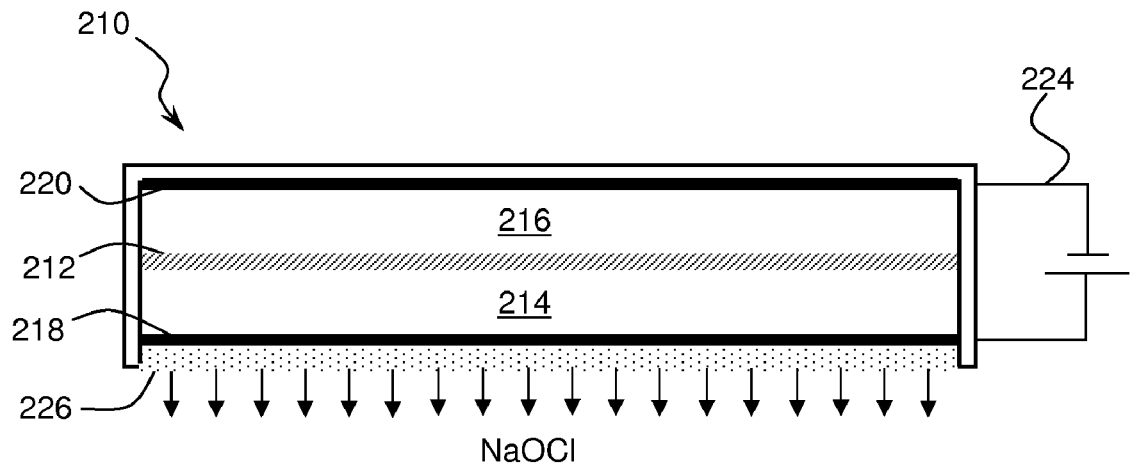
FIG. 5 is a schematic representation of a system to generate and dispense a cleansing agent at the point-of-use in the form of a topical skin patch, a scrub brush, or a floor brush or mop.

FIG. 5 is a schematic representation of a system to generate and dispense a cleansing agent at the point-of-use in the form of a topical skin patch, a scrub brush, or a floor brush or mop. The cleansing agent generator 210 shown in FIG. 5 has similar components to the apparatus illustrated in FIG. 1 and may be used to produce sodium hypochlorite. The cleansing agent generator 210 comprises an electrolytic cell that uses a sodium ion conductive ceramic membrane 212 that divides the electrochemical cell into two compartments: an anolyte compartment 214 and a catholyte compartment 216. An electrochemically active anode 218 is housed in the anolyte compartment 214 where oxidation reactions take place, and an electrochemically active cathode 220 is housed in the catholyte compartment 216 where reduction reactions take place. The sodium ion conductive ceramic membrane 212 selectively transfers sodium ions from the anolyte compartment 214 to the catholyte compartment 216 under the influence of an electrical potential 224 while preventing water transportation from either compartment to the other side. It may be advantages to include one or more conventional buffering agents, such as $NaHCO_3$, within the anolyte compartment 214 to control the operating pH.

The cleansing agent generator 210 comprises a porous membrane 226 which allows cleansing agent to pass from the anolyte compartment 214 to the exterior of the device. The porous membrane may define an active cleansing surface. It will be appreciated that the cleansing agent generator may be configured for use in scrub brush, or a floor brush by adding a handle. The generator may be constructed with thin flexible membranes and provided with suitable skin adhesive material for use as a topical skin patch.

The cleansing agent generator 210 may be configured for one-time batch use or it may be configured to permit replenishment of the anolyte and catholyte compartments for continuing use or repeated use.

Figure 6:
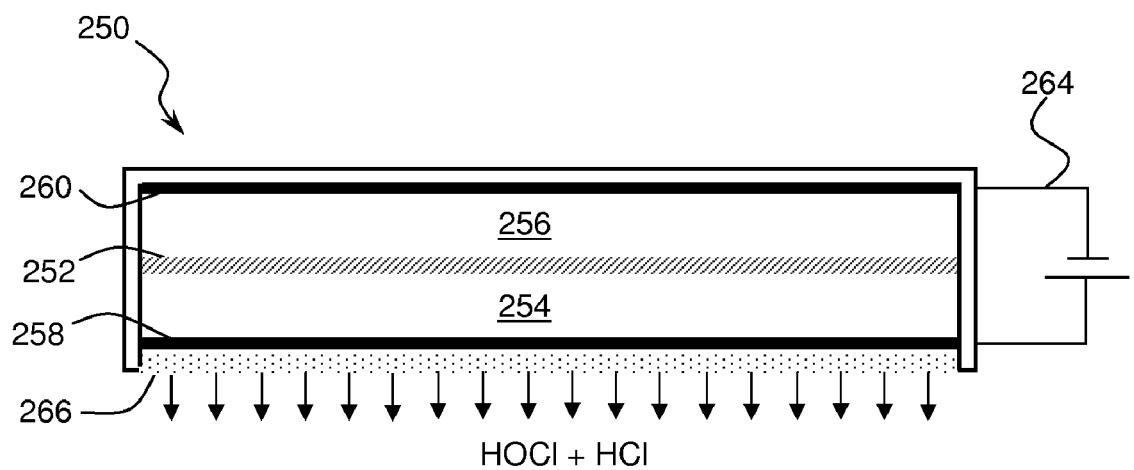
FIG. 6 is another schematic representation of a system to generate and dispense a cleansing agent at the point-of-use in the form of a topical skin patch, a scrub brush, or a floor brush or mop.

FIG. 6 is a schematic representation of a system to generate and dispense a cleansing agent at the point-of-use in the form of a topical skin patch, a scrub brush, or a floor brush or mop similar to the embodiment illustrated in FIG. 5. The cleansing agent generator 210 shown in FIG. 6 has similar components to the apparatus illustrated in FIG. 2 and may be used to produce hypochlorous acid. HCl may also be produced concurrently with the hypochlorous acid as a mixed oxidant stream. The cleansing agent generator 250 comprises an electrolytic cell that uses an anion conductive membrane 252 that divides the electrochemical cell into two compartments: an anolyte compartment 254 and a catholyte compartment 256. An electrochemically active anode 258 is housed in the anolyte compartment 254 where oxidation reactions take place, and an electrochemically active cathode 260 is housed in the catholyte compartment 256 where reduction reactions take place. The anion conductive membrane 252 selectively transfers chloride ions from the anolyte compartment 254 to the catholyte compartment 256 under the influence of an electrical potential 264. It may be advantages to include one or more conventional buffering agents within the anolyte compartment 254 to control the operating pH and promote the formation of HOCl.

The cleansing agent generator 250 comprises a porous membrane 266 which allows hypochlorous acid cleansing agent to pass from the anolyte compartment 254 to the exterior of the device. The porous membrane may define an active cleansing surface. It will be appreciated that the cleansing agent generator may be configured for use in scrub brush, or a floor brush by adding a handle. The generator may be constructed with thin flexible membranes and provided with suitable skin adhesive material for use as a topical skin patch.

The cleansing agent generator 250 may be configured for one-time batch use or it may be configured to permit replenishment of the anolyte and catholyte compartments for continuing use or repeated use.

The following non-limiting example is provided below which discusses the construction and use of a specific embodiment within the scope of the present invention. This embodiment is exemplary in nature and should not be construed to limit the scope of the invention in any way.

EXAMPLE 1

An apparatus to provide bleach (NaOCl) to a washing machine is prepared. The washing machine value is approximately 10 gallons. The amount of bleach to be added to a typical wash cycle is 50 ml of 5 wt. % NaOCl, which corresponds to 2.5 g of 100% bleach. The concentration of the bleach in the washing machine is about 0.007 wt. % bleach in 10 gallons of water. If the washing machine fills in five minutes, the cleansing agent generator must operate to produce NaOCl at a rate which results in 0.007 wt. % bleach through the cycle. To operate at this rate, the cleansing agent generator should comprise an electrolytic cell of the type described herein having a volume of about 100 $cm^3$ and active electrode area of about 100 $cm^2$. The anolyte NaCl concentration in water is >18 wt. %, and the catholyte NaOH concentration is water is >9.5 wt. %. Operating at 20 amps at 12 volts, the cell produces 50 $cm^3$ of 5 wt. % NaOCl in five minutes, sufficient to meet the requirements of the washing machine.

From the foregoing, it will be appreciated that the present invention provides a point-of-use electrochemical generator and dispenser of cleansing, sanitizing, and antimicrobial agents such as sodium hypochlorite and hypochlorous acid. The system to generate and dispense the cleansing agent at the point-of-use includes an electrolytic cell, such as those described herein, which produce sodium hypochlorite or hypochlorous acid as needed and a controller to efficiently control the operation of system. The cleansing agent may be generated on demand and used in household, industrial, and water treatment applications. The cleansing agent may be used in various types of apparatuses such as a washing machine, a dishwasher, a scrub brush, a floor brush or mop, a toilet bowl apparatus, topical skin patch, fruit or vegetable washing apparatus, or any application where a dose of a cleansing agent is desired.

While specific embodiments of the present invention have been illustrated and described, numerous modifications come to mind without significantly departing from the spirit of the invention, and the scope of protection is only limited by the scope of the accompanying claims.

The invention claimed is:
1. A system to generate and dispense a cleansing agent at the point-of-use comprising:
   an electrolytic cell configured to generate a cleansing agent comprising:
      an anode in an anolyte compartment comprising anolyte solution, wherein the cleansing agent is generated in the anolyte compartment;

a cathode in a catholyte compartment comprising catholyte solution; and a cleansing agent discharge opening to remove the cleansing agent generated in the anolyte compartment at the point-of-use;

a power source to supply electric current to the electrolytic cell;

a controller electrically coupled to the electrolytic cell and to the power source to control the rate and amount of cleansing agent generated; and wherein the electrolytic cell generates HOCl and comprises a chlorine ion conductive membrane.

2. The system according to claim 1, further comprising a feeder to resupply one or more of the catholyte compartment or anolyte compartment with catholyte solution or anolyte solution.

3. The system according to claim 1, wherein the controller comprises one or more sensors to determine anolyte solution requirements in the anolyte compartment or catholyte solution requirements in the catholyte compartment.

4. The system according to claim 3, wherein the controller is coupled to a feeder to resupply one or more of the catholyte compartment or anolyte compartment with catholyte solution or anolyte solution according to the anolyte or catholyte solution requirements.

5. The system according to claim 1, wherein the controller comprises one or more sensors to determine whether sufficient cleansing agent is produced.

6. The system according to claim 1, wherein the controller comprises one or more sensors to determine whether the cleansing agent produced satisfies cleansing agent requirements.

7. The system according to claim 1, wherein the anolyte compartment comprises a porous membrane having an interior surface in contact with cleansing agent produced within the anolyte compartment and an exterior surface, such that cleansing agent produced within the anolyte compartment passes through the porous membrane for direct use at the exterior surface.

8. The system according to claim 7, wherein the system is configured as a scrub brush or floor brush.

9. The system according to claim 7, wherein the system is configured as a topical skin patch, comprising flexible membranes and a skin adhesive.

10. The system according to claim 1, wherein the controller is coupled to the cleansing agent discharge opening to control the amount of cleansing agent dispensed directly to an appliance.

11. A system to generate and dispense a cleansing agent at the point-of-use comprising:

an electrolytic cell configured to generate a cleansing agent comprising:

an anode in an anolyte compartment comprising anolyte solution, wherein the cleansing agent is generated in the anolyte compartment and the cleansing agent is selected from NaOCl and HOCl;

a cathode in a catholyte compartment comprising catholyte solution; and a cleansing agent discharge opening to remove the cleansing agent generated in the anolyte compartment at the point-of-use;

a power source to supply electric current to the electrolytic cell;

a feeder to resupply one or more of the catholyte compartment or anolyte compartment with catholyte solution or anolyte solution;

a controller electrically coupled to the electrolytic cell, to the power source, to the feeder, and to a plurality of sensors, wherein the controller controls the rate and amount of cleansing agent generated, wherein the controller determines anolyte solution requirements in the anolyte compartment or catholyte solution requirements in the catholyte compartment, wherein the controller resupplies one or more of the catholyte compartment or anolyte compartment with catholyte solution or anolyte solution according to the anolyte or catholyte solution requirements; and, wherein the electrolytic cell generates HOCl and comprises a chlorine ion conductive membrane.

12. The system according to claim 11, wherein the controller comprises one or more sensors to determine whether sufficient cleansing agent is produced.

13. The system according to claim 11, wherein the controller comprises one or more sensors to determine whether the cleansing agent produced satisfies cleansing agent requirements.

14. The system according to claim 11, wherein the controller is coupled to the cleansing agent discharge opening to control the amount of cleansing agent dispensed directly to an appliance.

* * * * *